United States Patent [19]

Lading et al.

[11] Patent Number: 5,143,934

[45] Date of Patent: Sep. 1, 1992

[54] METHOD AND COMPOSITION FOR CONTROLLED DELIVERY OF BIOLOGICALLY ACTIVE AGENTS

[75] Inventors: Pia Lading, Gentofte, Denmark; Yvonne Lundsholm, Oxie, Sweden; Tomas Norling, Copenhagen, Denmark

[73] Assignee: A/S Dumex (Dumex Ltd.), Copenhagen, Denmark

[21] Appl. No.: 424,416

[22] Filed: Oct. 20, 1989

[51] Int. Cl.$^5$ ................................ A61K 31/415
[52] U.S. Cl. .................... 514/396; 424/435; 424/423; 424/484; 424/195.1; 514/943; 514/944; 514/964
[58] Field of Search ............ 514/396, 943, 944, 964; 424/435, 443, 195.1, 407, 423, 484

[56] References Cited

U.S. PATENT DOCUMENTS

| | | | |
|---|---|---|---|
| 2,196,322 | 4/1940 | Nitardy | 524/195.1 |
| 4,568,535 | 2/1986 | Loesche | 424/435 |
| 4,698,359 | 10/1987 | Niederer | 514/396 |

FOREIGN PATENT DOCUMENTS

| | | |
|---|---|---|
| 0244118 | 11/1987 | European Pat. Off. |
| 0126751 | 5/1988 | European Pat. Off. |

OTHER PUBLICATIONS

Lewkowtsch, Chemical Analysis of Oils Fats & Waxes 1898 pp. 385-389.
Balmbra, R. R. Nature 222 1969 pp. 1159-1160.
Goodson et al., J. Clin. Periodon. 6, 83-92 (1979).
Lindhe et al., J. Clin. Periodon. 6, 141-149 (1979).
Dunn et al., Proceed. Intern. Symp. Control Rel. Bioact. Mater. 14 259-260 (1987).
Minabe et al., J. Clin. Periodont. 16. 291-294 (1989).
Addy et al., Periodontol. 53. 693-699 (1982).
Golomb et al., J. Dent. Res. 63, 1149-1153 (1984).
Baker et al. Proceed. Intern. Symp. Control Rel. Bioact Mater. 15, 238 a–238 b (1988).
Gutman et al., Surfactants in Solution, vol. 1 (ed. K. L. Mitt and B. Lindman) Plenum Pub. Corp., 1984, p. 143-152.
Lindstrom et al., Lipids, 16, 749-754 (1981).
Landh et al., "Water System-A Drug Delivery Sytem". Abstract, Bioscience, Lund, Sweden (Apr. 23-26, 1989).
Landh et al., "Aqueous Dispersions of the Cubic Liquid Crystalline Phase in the Monoclein–Lectin Water System-A Drug Delivery System" Abstract, Bioscience, Lund, Sweden (Apr. 23-26, 1989).
Landh et al., (Untitled) Abstract, Abo, Finland (Jun. 10-11, 1989).

*Primary Examiner*—Ronald W. Griffin
*Assistant Examiner*—Ralph Gitomer
*Attorney, Agent, or Firm*—Seidel, Gorda, Lavorgna & Monaco

[57] ABSTRACT

Controlled delivery of biologically active agents such as pharmaceuticals to body sites is accomplished by combination with a monoglyceride and a vegetable oil. Upon contact with an aqueous liquid, the composition forms a reverse hexagonal liquid crystalline phase matrix which releases the active agent in controlled fashion. The method of delivery is particularly useful for the treatment of periodontal disease by insertion of the liquid crystalline phase precursor composition directly into the periodontal pocket, where water from the gingival fluid induces the spontaneous in situ formation of the reverse hexagonal liquid crystalline phase matrix.

25 Claims, 3 Drawing Sheets

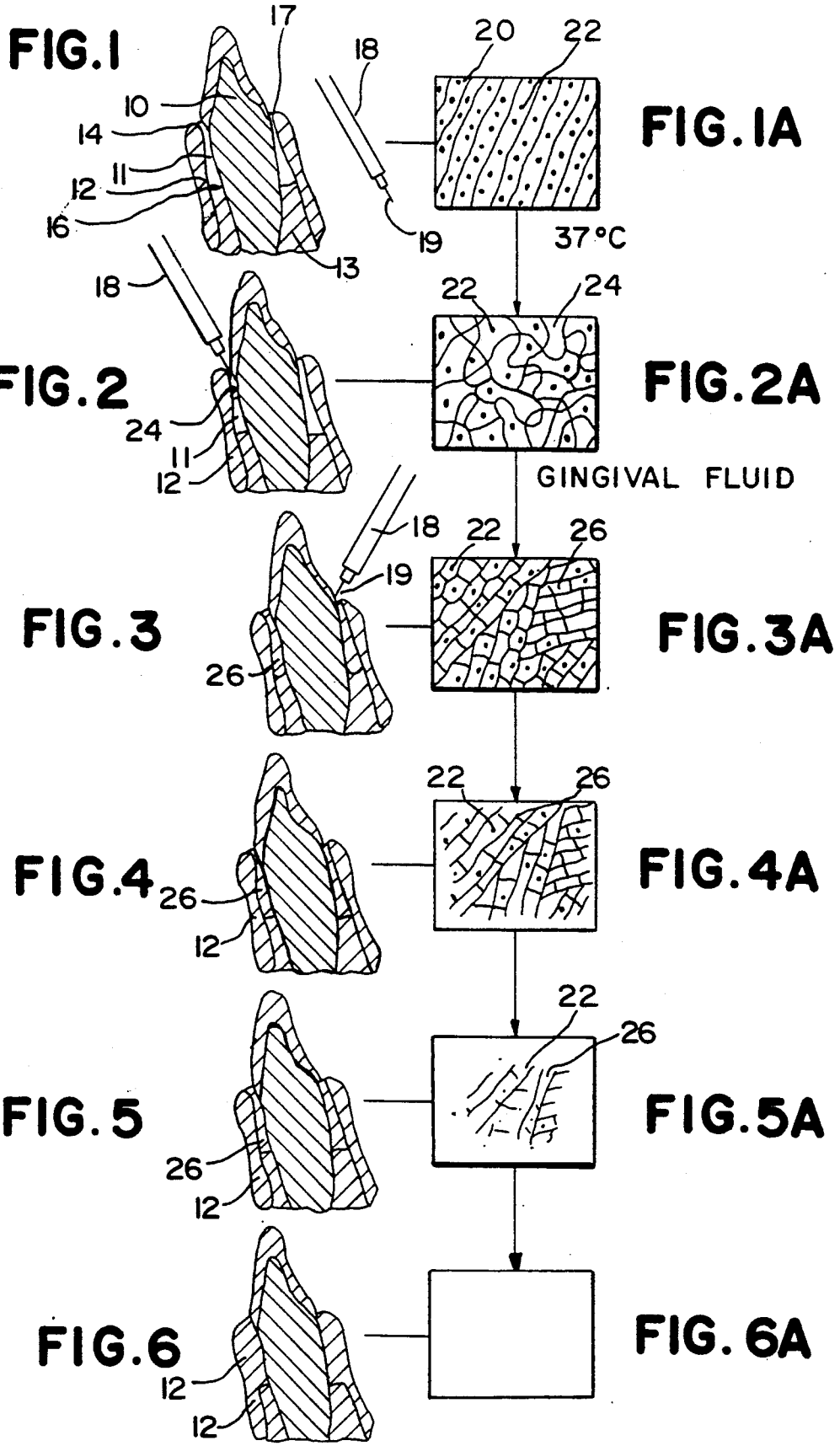

METHOD AND COMPOSITION FOR CONTROLLED DELIVERY OF BIOLOGICALLY ACTIVE AGENTS

FIELD OF THE INVENTION

The invention relates to the field of controlled release of biologically active agents, particularly pharmaceuticals, to body sites of animals and humans. The invention relates in particular to the treatment of periodontal disease through controlled release of such agents to the periodontal disease lesion.

BACKGROUND OF THE INVENTION

Various pathological conditions are characterized by the attack of microbes on body tissues, resulting in local inflammation and the appearance of lesions characterized by tissue destruction at the infection site. The result of the accumulated tissue destruction may be a characteristic cavity or gap in the tissue, which may become enlarged as the infection and inflammation progresses.

Periodontal disease, in particular, is characterized by this course. Periodontal diseases comprise the various pathological conditions which are clinically and histologically detectable as inflammation of the periodontal tissues. The latter are collectively comprised of the gingiva, cementum, periodontal ligament, and alveolar bone. Periodontal diseases are caused by bacterial colonization of the surfaces of the teeth, and may be complicated by other hosts and causative factors. The disease is common in humans as well as in animals. Untreated periodontal disease causes loss of teeth which compromises the integrity and function of the masticatory system.

It is well documented that the progression of periodontal disease through various stages of severity begins with an accumulation of bacteria, termed plaque, on the tooth surface in the marginal area of the gingiva. See, for example, Rateitschak et al., Color Atlas of Periodontology (1985). The response to this formation of microbial plaque is an inflammation of the gingiva and the resulting breakdown of tissues, which causes the formation of an opening along the tooth surface known as the "periodontal pocket". As the bacterial colonization of the pocket and the inflammatory processes continue, the destruction of the periodontal tissues progresses and the tooth becomes loose. Once deprived of supporting tissues, which will not regenerate, the tooth will eventually be lost. The infection is local. The same patient may have entirely healthy teeth immediately proximal to the diseased tooth.

One treatment for removing periodontal disease aims to remove the bacteria from the tooth's surface and the pockets by mechanical means. Using various instruments such as curettes, sickles, hoes, files, etc., the bacteria are removed from the infected areas by scraping the teeth and pockets, one by one. Such mechanical procedures are very time consuming. Each tooth takes about 5-15 minutes to treat. The discomfort and pain for the patient are considerable. Mechanical removal of bacteria is a method of therapy which requires highly skilled dental operators. The procedure may be difficult to perform, particularly if the pockets are deep, and are presented with root fissures or furcations. In order to improve mechanical removal, the accessibility and visibility of the root surface may be facilitated by surgical procedures such as flap operations.

Since bacteria are involved in the etiology and progression of periodontal disease, antibacterial drugs have also been utilized in periodontal therapy. An effective concentration of an antibacterial drug at the site of infection may be achieved by the systemic administration of a high dosage of the drug. In order to maintain an effective concentration over an extended period of time, it is necessary to repeat the dosage 2-3 times daily for several weeks. Long term exposure to high dosages of antibiotics is associated with a high risk of side effects, a fact that has seriously limited the use of this treatment in periodontal therapy.

A better way to obtain an effective drug concentration at the site of infection is to apply the drug directly to the periodontal pocket. According to this methodology, only the amount of drug locally required is administered. The total dosage of the drug is thus reduced considerably. However, in order to maintain an effective concentration of drug for an extended period of time (days to weeks), the drug-containing system must be retained within the pocket, and the drug must be released slowly therefrom.

Delivery systems for controlled release of drugs into the periodontal pocket fall generally within two categories: (1) solid drug-containing devices which are inserted into the pocket, or (2) thermodynamically unstable, fluid systems such as suspensions, emulsions, vesicles, and the like which are delivered into the pocket through fine tubings, such as needles and the like.

Examples of the solid drug-containing category of devices are the tetracycline-filled, hollow fibers that are tied around the tooth and pressed down below the gingiva. Such systems are described, for example, in Goodson et al., J. Clin. Periodon. 6, 83-92 (1979); Lindhe et al., J. Clin. Periodon. 6, 141-149 (1979); and Dunn et al. Proceed. Intern. Symp. Control Rel. Bioact. Mater. 14, 259-260 (1987). Other types of solid drug-containing devices comprise strips formed of drug-containing polymeric materials which are cut into shape and placed into the pocket, with, for example, tweezers: Addy et al., J. Periodontol. 53, 693-699 (1982); Golomb et al., J. Dent. Res. 63, 1149-1153 (1984); U.S. Pat. No. 4,568,535; and Minabe et al., J. Clin. Periodont. 16, 291-294 (1989). Such devices are difficult to manipulate, and may be lost accidentally during normal oral functions. Their insertion is timeconsuming, and the presence of a foreign body may induce or aggravate inflammatory processes.

Fluid periodontal delivery systems are described by Baker et al., Proceed. Intern. Symp. Control Rel. Bioact. Mater. 15, 238a-238b (1988) and European Patent Application 244,118 (1987). Microparticles are produced by dispersing or coating the drug with a release-controlling polymer. The microparticles are then suspended in a paste or gel and placed in the periodontal pocket with a syringe and rubber tube. One of the drawbacks of such systems is the limited shelf life due to the leaking of the drug from the particles once they are suspended in the carrier medium. Another disadvantage is the poor retention of the suspension within the periodontal pocket for a period of time long enough to result in successful treatment. The flow of gingival exudate in the inflamed pocket is considerable, and tends to wash away such particles.

A unique controlled-release preparation for delivery of biologically active materials has been proposed in European Patent Specification 126,751 B1. According to the invention described therein, a biologically active material is provided in mixture with an amphiphilic substance capable of forming a cubic or other type of liquid crystal-line phase when placed in contact with a liquid selected from the group of water, glycerol, ethylene glycol and propylene glycol. The cubic liquid crystalline phase is characterized as a thermodynamically stable, viscous and optically isotropic phase formed of the amphiphilic substance and water. The cubic phase may be unambiguously identified from the X-ray diffraction pattern. Other liquid crystalline phases, such as the hexagonal and reverse hexagonal phase, may be formed which, like the cubic phase, are described as being useful for drug delivery. The bioactive material is dissolved or dispersed in the liquid crystalline phase composed of water and the amphiphilic compound.

While the invention described in the aforesaid European Patent Specification represents an advance in the state of the art of controlled release delivery, such compositions have not been heretofore utilized for the formation of controlled release matrixes in situ at body sites, nor have they been used for the treatment of periodontal disease.

SUMMARY OF THE INVENTION

According to one aspect, the invention is directed to a composition for delivery of a biologically active agent to a body site in an animal or human comprising at least one monoglyceride and at least one vegetable oil in amounts sufficient to form a reverse hexagonal liquid crystalline phase when in contact with an aqueous liquid, and an effective amount of the biologically active agent dispersed therein. The composition is solid at about room temperature, but has a melting point below about body temperature.

According to another aspect, the invention is directed to a method for controlled delivery of a biologically active agent to a body site in an animal or human. The above composition is discharged from a dosing device into a body site, wherein it combines with aqueous liquid from the body site to form a reverse hexagonal liquid crystalline phase which releases the active agent to the body site in a controlled fashion. The novel composition combines with the aqueous liquid in an in situ curing process, which results in the formation of the reverse hexagonal liquid crystalline phase. In a preferred embodiment, the method is directed to treatment of periodontal disease, wherein the composition is delivered to the periodontal pocket.

In yet another embodiment, the invention is directed to an article of manufacture comprising a dosing device adapted for delivery of biologically active agents to body sites. The dosing device contains a composition which is solid at room temperature, and which has a melting point below about body temperature. The composition comprises an effective amount of at least one biologically active agent, and at least one monoglyceride and at least one vegetable oil in amounts sufficient to form a reverse hexagonal liquid crystalline phase when placed in contact with an aqueous liquid. The crystalline phase releases the active agent to the body site in a controlled manner.

The term "biologically active agent" as used in the herein specification and appended claims means any compound or composition which has utility in the treatment or prevention of disease or disorders affecting animals or humans, or in the regulation of any animal or human physiological condition. In its broadest aspect, the term "biologically active agent" refers to any compound or composition which, when administered in an effective amount, has an effect on living cells or organisms.

The term "aqueous liquid" as used herein means water, or any liquid comprising water at least in part. Such liquids include, in particular, any of the various body fluids or secretions containing water which, when placed in contact with the composition of the invention, induces the in situ formation of the reverse hexagonal liquid crystalline phase.

The term "liquid crystalline phase" as used herein has the same meaning as stated in European Patent Specification 126,751 B1, namely, it is used to denote an intermediate state between solid crystals and isotropic liquids, characterized by long-range order and short-range properties close to those of a simple liquid or solution (Keller et al., Handbook of Liquid Crystals, Verlag Chemie, Weinheim, Germany (1980)). The terms "cubic liquid crystalline phase" and "cubic phase" as used herein have the same meaning as set forth in European Patent specification 126,751 B1, namely, they are used herein to mean a thermodynamically stable, viscous and optically isotropic phase made of at least one amphiphilic substance and water. The cubic phase may be unambiguously identified from its X-ray diffraction pattern.

The terms "hexagonal liquid crystalline phase" and "reverse hexagonal liquid crystalline phase" as used herein mean thermodynamically stable, viscous and optically anisotropic phases characterized by long-range order in two dimensions formed of at least one amphiphilic substance and water. The hexagonal phases may be identified by their X-ray diffraction patterns. The "reverse hexagonal" crystalline phase, while giving the same X-ray diffraction pattern as the hexagonal phase, is readily distinguished from the latter by its behavior upon increasing water dilution. While the hexagonal phase may be diluted with water, the reverse hexagonal phase will absorb water to a point. Further addition of water results in the creation of a separate water phase outside the crystalline phase. This is because the reverse hexagonal crystalline phase is characterized by water-containing cylinders formed by amphiphilic molecules—the opposite of the normal hexagonal crystalline phase.

DESCRIPTION OF THE FIGURES

FIGS. 1, 1A, 2, 2A, 3, 3A, 4 4A, 5, 5A, 6 and 6A show the steps of the practice of the present invention in treating periodontal disease as applied to a single tooth, shown in cross-section. Changes in the physical state of the composition utilized to fill the periodontal pocket are indicated schematically in the boxes.

DETAILED DESCRIPTION OF THE INVENTION

Figure 7:
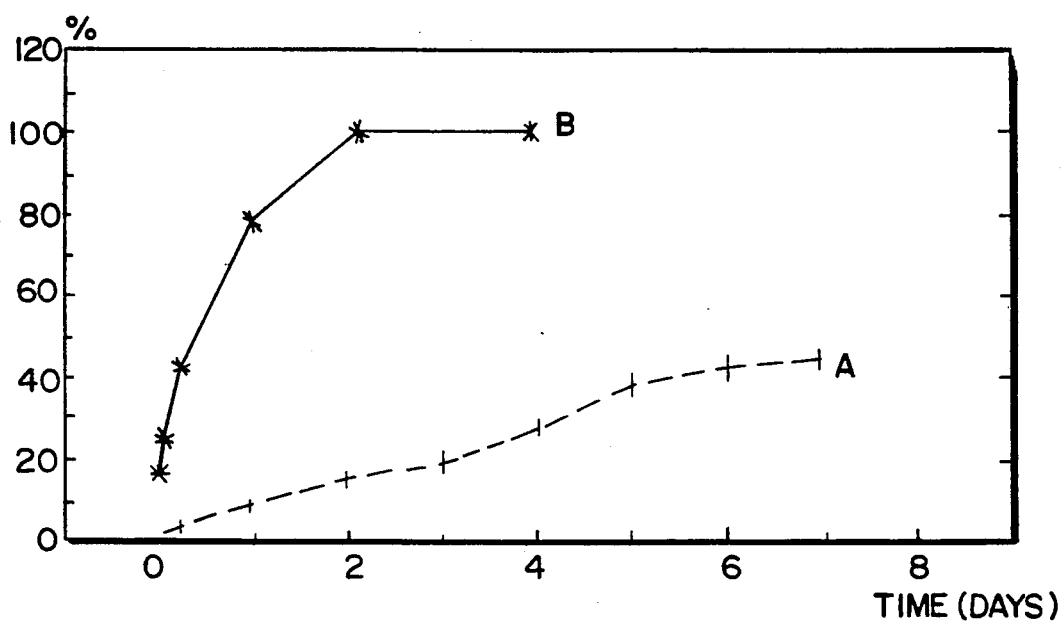
FIG. 7 is a plot of the in vitro release profile of two metronidazole-containing compositions characterized by the reverse hexagonal liquid crystalline phase.

The composition of the invention include one or more biologically active agents and one or more monoglycerides and vegetable oils. The monoglyceride and vegetable oil are present in an amount capable of forming a reverse hexagonal liquid crystalline phase when contacted with an aqueous liquid. The reverse hexagonal liquid crystalline phase, unlike the fluid systems which have heretofore been utilized for delivery of drugs to the periodontal pocket, is thermodynamically stable. Because of its thermodynamic stability, highly reproducible controlled-release systems are possible with the reverse hexagonal liquid crystalline phase.

The composition is a stable solid at room temperature (about 22° C-25° C.) and below, but melts at a temperature below about normal body temperature (about 37° C). The composition is characterized as being a precursor for the formation of the reverse hexagonal liquid crystalline phase. When in the precursor state, the composition has the form of a highly stable solid matrix which contains the biologically active agent uniformly dispersed therein. The uniformity of the drug dispersion is substantially constant over prolonged periods of storage. The composition is, however, sufficiently deformable so as to be extrudable from a suitable dosing device into the target body site.

When the composition is placed in the periodontal pocket or the other body site wherein water is present, a reverse hexagonal liquid crystalline phase will be formed spontaneously in situ, rendering the product into a highly viscous mass which is retained within the periodontal pocket or other body site. The matrix of this liquid crystalline phase forms a diffusion barrier which effectively controls the rate of drug release to the body site.

The monoglycerides which may be utilized in forming the reverse hexagonal liquid crystal phases in the present invention include, for example, glycerol monooleate and glycerol monolinoleate.

Solid glycerol monooleate exists in several crystalline modifications, each having a different melting point. The modification with the highest melting point, the $\beta$-form, is thermodynamically stable. Thus, the $\beta$-form is the preferred crystalline form, as no changes in the composition will occur during storage. The $\beta$-crystalline form is obtained following mixing of the composition components (drug, monoglyceride and vegetable oil) by cooling to a temperature of about 20°-22° C., which is just below the melting point of the $\beta$-form.

It is known that water and amphiphilic substances such as monoglycerides spontaneously associate to form, thermodynamically stable micellar, cubic, hexagonal and lamellar phases, in the presence of an increasing amount of amphiphile. Each phase is characterized by distinct hydrophilic and hydrophobic domains. Moreover, while it is known that the occurrence of the reverse hexagonal liquid crystalline phase may be induced in water/monoglyceride systems at high temperature (above 40° C.), or by the addition of, for example, phospholipids, the phase has been observed to exist only across a relatively narrow range of monoglyceride concentration. The relatively narrow range of monoglyceride concentration necessary to achieve the phase renders reproducability difficult. This is unfortunate, since of all the various phases of physical associations of amphiphilic/water systems—micellar, cubic, hexagonal, reverse hexagonal and lamellar,—the reverse hexagonal is the most attractive as a matrix for controlled release of pharmaceuticals. In the reverse hexagonal phase, the hydrophilic regions of the crystal are internal, and the hydrophobic regions are external. A biologically active agent entrained in the matrix of the reverse hexagonal liquid crystal phase will be released only slowly from the matrix, as water diffuses therethrough. This phase is preferred over the cubic phase, since while it is highly viscous, it is not as viscous as the cubic phase, and has superior controlled release characteristics over the cubic phase.

We have found that when an amount of vegetable oil is added to the monoglyceride/water system containing as a fourth component a biologically active agent, the occurrence of the reverse hexagonal liquid crystalline phase as a function of monoglyceride concentration is markedly increased, and the phase is observed to occur at body temperature (about 37° C.), and at temperatures as low as about 20° C. The invention thus makes practically possible the controlled release of biologically active agents to body sites using monoglyceride/water liquid crystal systems, at physiologic temperatures.

The vegetable oils useful in the practice of the present invention include fixed oils of vegetable origin. By "fixed oil", is meant, of course, an oil which does not evaporate under ordinary conditions. Thus, the fixed oils used in the practice of the invention are the nonvolatile, fatty oils characteristic of vegetables, as opposed to the volatile essential oils derived from flowers.

Fixed oils of vegetable origin consist mainly of triglycerides, i.e., fatty esters of glycerol, which may be simple triglycerides, in which the free hydroxyl groups of glycerol are esterified with the same acid, or mixed triglycerides, in which two or three different acids may be esterified. The fixed vegetable oils may be extracted from the seeds, fruit or nuts of plants. They include, for example, cotton seed oil, safflower oil, corn oil, sesame oil, almond oil, poppy seed oil, olive oil, peanut oil, rape seed oil, soybean oil, and the like, or purified or refined vegetable oils such as the triglycerides available from Dynamit Nobel Wien GmbH under the trademark Miglyol ®. Other fixed vegetable oils are known to those skilled in the art. Sesame oil is particularly useful in the practice of the present invention.

Unlike many controlled release systems for the delivery of pharmaceuticals, the composition of the invention which is characterized by a reverse hexagonal liquid crystalline phase formed between water, monoglyceride and vegetable oil, releases drug in a pH independent manner. This is significant since the pH may vary from body site to body site. Moreover, the pH may vary over time at a single body site. Stability of release rate to changes in pH is particularly attractive in dental and periodontal applications, since the pH of the mouth may fluctuate radically depending upon the nature of the foods and liquids ingested by the patient during the course of treatment.

The biologically active agents may comprise any agent or agents which are usefully administered to a body site for the prevention or treatment of disease, or other biological effect or condition. Such active agents, including those which may be delivered to the periodontal pocket, are listed as follows by way of illustration, and not by way of limitation:

Antiseptic agents such as chlorhexidine, thiomersal, phenols, chloramine, iodoform, hydrogen peroxide; antibacterial agents such as $\beta$-lactam antibiotics including, e.g., penicillins, ampicillin, amoxycillin, cephalosporins, cefotaxime, floxomef, cefalotin, monobactams, aztreonam, thienamycin and their derivatives; quinolones such as ofloxacin, enoxacin, norfloxacin, perfloxacin, ciprofloxacin, etc.; aminoglycosides, such as gentamicin, tobramycin, sisomicin, netilmicin, kanamycin etc; tetracyclines; erythromycin; lincomycin; roxithromycin; clindamycin; chloramphenicols; bacitracins; polymyxins; sulphonamides; metronidazole; tinidazole; nimorazole; ornidazole; fusidin; fosfomycin; antifungal agents such as amphotericin, nystatin, miconazole, ketoconazole, bifonazole, tioconazole, fluconazole, natamycin, etc.; cytotoxic substances including, e.g., 5-fluororacil, hydroxyurea, cytarabin, thiotepa, cyclosporin, etc.; anti-inflammatory agents such as hydrocortisone, prednisolone, betamethasone, dexamethasone, fluocortolone, and other steroids; nonsteroidal anti-inflammatory drugs including, e.g., indomethacin, ibuprofen, ketoprogen, piroxicam, flurbiprofen, naproxen, acetylsalicylic acid, and phenylbutazone; antiplaque agents including muramidases, amylases, dextranases, octapinol, and decapinol; growth factors including, e.g., platelet-derived growth factor and insulin-like growth factor; collagenase inhibitors; inhibitors of bone resorption or osteoclast activity such as etiodronate, clodronate, calcitonin, etc.; local anesthetics such as lidocaine, procaine, xylocaine, etc.; and so on.

Most preferably, the biologically active agent is an antibacterial agent useful for plaque control and the treatment of periodontal disease. Such agents, include, for example, tetracycline, chlorhexidine, metronidazole and metronidazole esters such as metronidazole benzoate.

The preferred antimicrobial agents for delivery to the periodontal pocket comprises metronidazole and its esters. It is known that gingivitis, an inflammation of the gingiva that is associated with poor oral hygiene, and periodontitis (periodontal disease), the form of gingivitis which has progressed to involve the destruction of oral tissues, are characterized by bacterial infestations increasingly dominated by anaerobic bacteria. Treatment of periodontal disease is therefore most effectively accomplished by use of an antibacterial agent such as metronidazole, which is active against anaerobic bacteria. See, for example, U.S. Pat. No. 4,568,535 disclosing incorporation of metronidazole in a polymer material, such as ethylcellulose, which is placed directly into the diseased periodontal pocket.

Prior to administration, the composition comprising the biologically active agent, the monoglyceride, and the vegetable oil is stored in a suitable dosing device. At room temperature, the composition as contained in the dosing device is in the solid state. Typically, the solid is in the form of a fairly rigid, paste-like gel, which is stable at room temperatures for prolonged periods. The gel maintains the biologically active agent uniformly dispersed therein. However, by virtue of the presence of vegetable oil, which serves as a plasticizing agent, the composition in this form maintains a sufficient level of pliability so as to be readily extrudable from the dosing device. The gel may be discharged from the dosing device into the targeted body site by any suitable means known to those skilled in the art.

Figure 8:
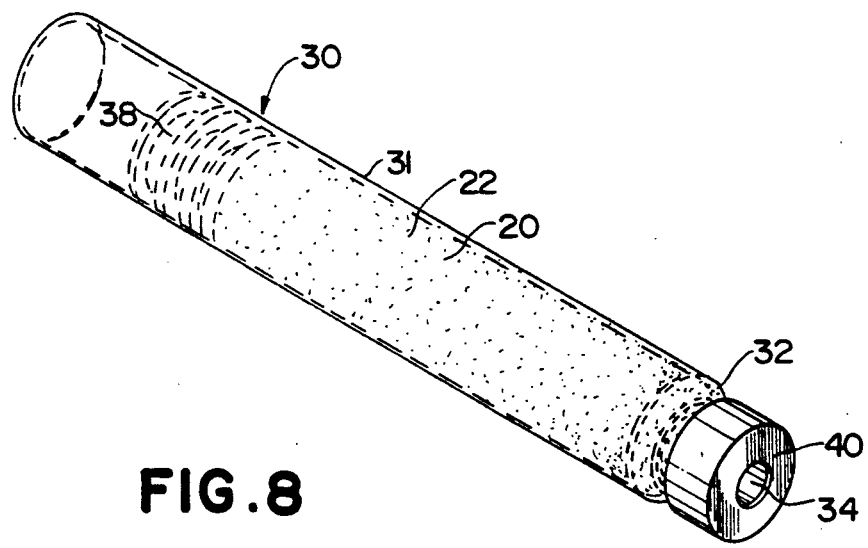
FIG. 8 is a perspective view of a typical dosing device which may be used in the practice of the invention.

Dosing devices suitable for delivering the composition to body sites include any of the dosing devices adapted for containing and mechanically releasing pharmaceutical materials. Generally, the dosing device is advantageously in the form of an ampule or cartridge suitable for use in conjunction with standard medical or dental syringes. Preferably, the dosing device is in the form of an ampule, such as the type in which local anesthetic is typically supplied to dentists and physicians. Such devices are well-known to those skilled in the art. A glass ampule of this type, generally designated as 30, is shown in FIG. 8. The ampule contains a stable paste-like solid matrix 20 with biologically active agent 22 dispersed therein. Ampule 30 has a cylindrical body 31, terminating in a discharging end 32, containing an opening (not shown) covered by a diaphragm 34 made of thin metal, rubber or other material which may be readily pierced by a hypodermic needle. Diaphragm 34 is secured to the discharging end of ampule 30 by cap 40. The other end of the cylindrical body is open, and is adapted to receive the plunger of a hypodermic syringe (not shown). A stopper 38 made of rubber or like material is movable within the cylindrical body and serves to retain matrix 20 in the ampule. In use, stopper 38 is propelled by the force of the syringe plunger toward the discharging end 32 of the ampule, and discharges the ampule's contents into the body site.

The composition of the invention may be conveniently applied from the dosing device to any body site where sufficient aqueous liquid is available to induce formation of the reverse hexagonal liquid crystalline phase, and where there is a need for a continuous local supply of biological agent. Alternatively, if the body site does not contain sufficient aqueous liquid from body fluids available at the site, formation of the reverse hexagonal phase may be triggered by the addition of exogenous water or other aqueous liquid.

The body site is advantageously in the form of a cavity, pocket or other indentation in the tissue in which the composition may be applied and collected. Such body sites include, for example, puncture wounds, incisions, sinuses, the outer ear, and other tissue spaces or voids. The invention has particular utility in dental applications, where it may be applied, for example, to the periodontal pockets, jawbone sockets following tooth extractions, root canals, and the like. In the case of tooth extractions, it will be recognized that systemically administered antibiotic may no longer reach the extraction site as a result of the tooth removal and termination of blood supply to the site. A local supply of antibiotic following extraction is therefore most desirable.

The aforementioned body sites are intended to be illustrative only. Other applications sites may include, for example, all of the various external body surfaces. The composition may be advantageous applied in the form of a plaster for application to the skin, either with or without adhesive means for assisting in the attachment of the material to the skin.

The matrix formed in situ as a result of the practice of the invention in completely biodegradable, as its primary component is lipid. The matrix, over time, is decomposed by the action of the body's own lipases. Thus, along with releasing the biologically active agent in a controlled fashion, the matrix will eventually decay and disappear from the body site. It may be readily appreciated that the rate of disappearance is related directly to the size and thickness of the implant.

The relative amount of the monoglyceride and the vegetable oil in the composition for formation of the reverse hexagonal liquid crystalline phase may vary over a considerable range. Generally, the vegetable oil is present in an amount sufficient to improve the flow characteristics of the composition upon release from the dosing device and induce the formation of a stable reverse hexagonal liquid crystalline phase upon contact with an aqueous liquid. Generally, the vegetable oil and monoglyceride are present in a weight ratio of from about 1:99 to about 30:70 vegetable oil to monoglyceride, preferably from about 1:99 to about 25:75, most preferably from about 5:95 to about 15:85, based upon the combined weight of the monoglyceride and vegetable oil. The amount of drug in the composition, hereinafter described as the "drug loading" may vary depending on the nature of the drug, the dosage desired, and the rate of release desired. Typically, the drug loading ranges from about 1 to about 50% by weight of the entire composition.

The specific amount of biologically active agent contained in the composition will of course, vary according to certain factors such as the nature of the active substance, and its potency; the amount required to bring about the desired therapeutic or other effect; the nature of the body site; and the like. By "effective amount" of the biologically active agent is meant an amount sufficient to achieve and maintain a therapeutic local level of the agent at the targeted body site over a desired period of time.

The composition of the invention may be formed by mixing the monoglyceride and vegetable oil components at elevated temperature, followed by cooling. Thereafter, the drug is added, and the composition is taken up in a suitable dosing device. Following contact with water, or other aqueous liquid, and the formation of the reverse hexagonal liquid crystalline phase, the viscosity of the resulting gel is very high, more than 350,000 cP measured at a shear rate of $0.3$ s$^{-1}$ in a Haake RV100 viscometer.

The practice of the invention is illustrated in its application to a periodontal pocket in FIGS. 1 through 6.

There is shown in FIG. 1 a periodontal-diseased tooth 10. The tooth is attached to the alveolar bone 13. A periodontal pocket 11 has been formed between the gum 12 and the tooth's root surface 15. The depth of the pocket is the difference between the height of the gingival margin 14 and the pocket's base 16. The cement-enamel junction of the tooth is indicated at 17. FIG. 1a is a schematic representation of the contents of a dosing device (not shown), such as the ampule 30 in FIG. 8, contained in a syringe 18. The syringe includes a flexible hypodermic needle 19. At this state, the composition is in the form of a paste-like solid 20 having dispersed uniformly therein the biologically active agent 22, as indicated in FIG. 1a.

In FIG. 2, the material is dispelled from the ampule-containing syringe 18 through flexible needle 19 inserted into the periodontal pocket 11. As the syringe is discharged, the composition becomes heated to body temperature (about 37° C.), and melts into a flowable liquid filling the pocket. At this point, the dispensed composition is in the form of a flowable liquid 24, as schematically represented in FIG. 2a. The liquid evenly distributes throughout the periodontal pocket, carrying the biologically active agent 22 dispersed therein.

Filling of the periodontal pocket continues in FIG. 3. However, as filling takes place, the liquid material contacts and combines with the available water from the gingival fluid, and undergoes a spontaneous phase change from flowable liquid to a visco-elastic solid matrix 26 characterized by a thermodynamically stable reverse hexagonal liquid crystalline phase. See FIG. 3a.

Once the liquid crystalline phase is in place in the periodontal cavity, diffusion of the biological agent 22 from the liquid crystalline matrix into the periodontal pocket begins in a highly controlled fashion. See FIG. 4a. The matrix 26 also begins to slowly decay under attack from lipases, as shown in FIG. 5a. Eventually, the matrix disappears and normal growth of gum 12 fills the former periodontal pocket, as represented in FIGS. 6 and 6a.

The practice of the invention is illustrated by the following non-limiting examples.

EXAMPLE 1

52.8 g glyceryl monooleate and 7.2 g sesame oil is heated to 50° C. and mixed. After cooling to 40° C., 40.2 g metronidazole benzoate (micronized to a particle size distribution of 90% particles between 5 and 50 μm), corresponding to 25 g metronidazole, was incorporated into the mixture by means of a simple stirrer. The resulting product was inserted into glass cartridges by a peristaltic pump and crystallized by cooling to 20°-22° C. The crystallized product comprises a precursor for a reversed hexagonal liquid crystalline phase, which, when exposed to water, swelled to form a highly viscous, sticky, anisotropic solid gel mass which slowly released the metronidazole benzoate. The in vitro release profile of the gel mass in phosphate buffer (pH 8.0) was determined with a Disho tester (a commercially available instrument for testing dissolution of drugs from pharmaceutical preparations). To maintain the total sink condition, 1500 ml of phosphate buffer was used for each cell. The flow rate was fixed at 20 ml per minute. In each cell, one gelatin capsule was placed, containing between 100 and 200 mg of the gel, equivalent to 40-80 mg metronidazole benzoate. 3 ml samples were periodically taken from each cell and analyzed at 320 nm on a Beckman spectrophotometer, and at 314 nm on a Philips spectrophotometer. The results are shown in FIG. 7, curve A.

EXAMPLE 2

A mixture of 7.48 g glycerol monooleate and 10.2 g sesame oil and 15 g metronidazole was prepared as described in Example 1. The product is a precursor for a reversed hexagonal liquid crystalline phase. The in vitro release profile, following the protocol of Example 1, is shown in FIG. 7, curve B. It may be appreciated from a comparison of curves A and B that the less soluble ester form of the active agent, metronidazole benzoate (curve A), is released at a slower rate than the more water-soluble unesterified form of the drug (curve B).

The clinical efficacy of the Example 1 and Example 2 compositions was compared with conventional mechanical treatment as follows.

Sixty-one patients presenting with moderate to severe periodontitis, and who had not received any antibiotic treatment or conventional therapy during the three-month period prior to the start of the trial, were selected. Each patient had at least one tooth in each quadrant having a pocket with a probed pocket depth of at least 5 mm. Recordings of pocket depths and bleeding on probing were made before treatment and again at 2, 4, 6 and 12 weeks after treatment. A decrease in pocket depth and reduction in bleeding are indicators of successful treatment. By use of a split mouth design, i.e., dividing the mouth into four quadrants (upper right, upper left, lower left and lower right) four different treatments were compared within the same subject.

Each patient received four treatments, i.e., one treatment in each quadrant, in randomized assignments.

The four treatments were as follows:

A. Example 1 composition (metronidazole, 25% dental gel), applied once a week for two weeks;

B. Example 2 composition (metronidazole, 15% dental gel), applied once a week for two weeks;

C. Composition of Example 2 (metronidazole, 15% dental gel), applied twice a week for two weeks; and D. Conventional therapy by instrumentation.

The results, set forth in Tables 1 and 2, indicate that treatments A and C are equal to that of conventional mechanical therapy over a period of three months, as determined by the mean reduction in periodontal pocket depths and mean reduction in bleeding upon probing.

TABLE 1

| TREATMENT | Mean reduction in pocket depths (mm) following therapy Time (Months) | | | |
|---|---|---|---|---|
| | 1 | 1.5 | 2 | 3 |
| A: 25% gel 1/week | 0.95 | 1.08 | 1.28 | 1.25 |
| B: 15% gel 1/week | 0.66 | 0.99 | 1.17 | 0.99 |
| C: 15% gel 2/week | 0.86 | 0.94 | 1.27 | 1.18 |
| D: Instrumentation | 1.01 | 1.14 | 1.34 | 1.31 |

TABLE 2

| TREATMENT | Mean reduction in bleeding on probing (%) following therapy Time (Months) | | | |
|---|---|---|---|---|
| | 1 | 1.5 | 2 | 3 |
| A: 25% gel 1/week | 16 | 15 | 22 | 23 |
| B: 15% gel 1/week | 10 | 11 | 17 | 10 |
| C: 15% gel 2/week | 20 | 20 | 21 | 20 |
| D: Instrumentation | 12 | 17 | 17 | 20 |

EXAMPLE 3

Experiments were conducted by varying the relative amounts of glycerol monooleate and sesame oil in the composition prepared according to Example 1, in the presence of increasing amounts of water, while maintaining the drug loading (40% metronidazole benzoate) constant. More than 100 compositions were prepared. The identity of the liquid crystalline phase was determined for each composition at 35° C. The data are represented in the partial three-component phase diagram of FIG. 9. A large area of reverse hexagonal phase ($H_{II}$) appears. Lamellar ($L_a$), cubic (C) and reverse micellar ($L_2$) phases are also apparent, as well as a two-phase region of cubic/water (C/W) and a three-phase region of reverse hexagonal/reverse micellar/water ($H_{II}/L_2/W$). Each phase also contains undissolved metronidazole benzoate as an additional phase. The composition of Example 1, before dilution with water, is indicated as point Q. The dotted line connecting point Q and point R, the theoretical water dilution limit, provides an indication of the Example 1 composition's phase behavior upon increasing dilution.

Figure 9:
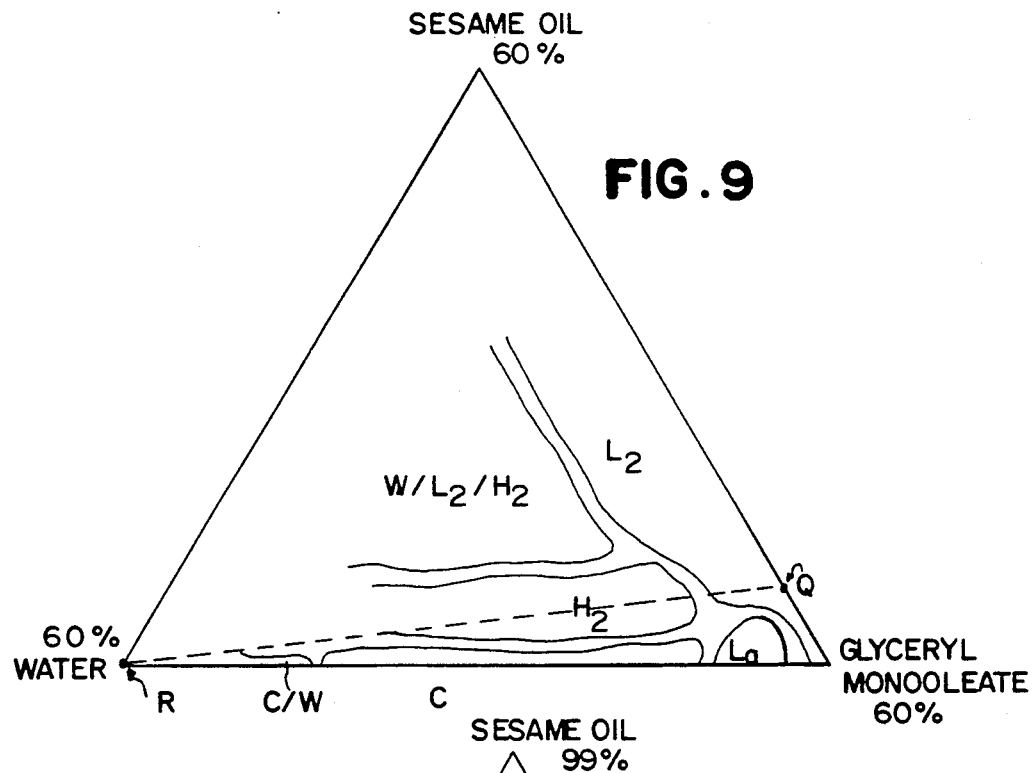
FIG. 9 is a partial three-component phase diagram created by varying the amounts of the components of a typical composition of the invention upon increasing dilution with water, while maintaining a constant drug loading (40% metronidazole benzoate).

It may be appreciated from a consideration of FIG. 9 that the present invention provides a controlled release drug delivery system characterized by the formation of a highly stable reverse hexagonal liquid crystalline phase upon contact with water. The relatively large size of the region of reverse hexagonal liquid crystalline phase, apparent from the ternary phase diagram, evidences the stability of the phase over substantial ranges of component concentration and increasing water dilution.

EXAMPLE 4

Figure 10:
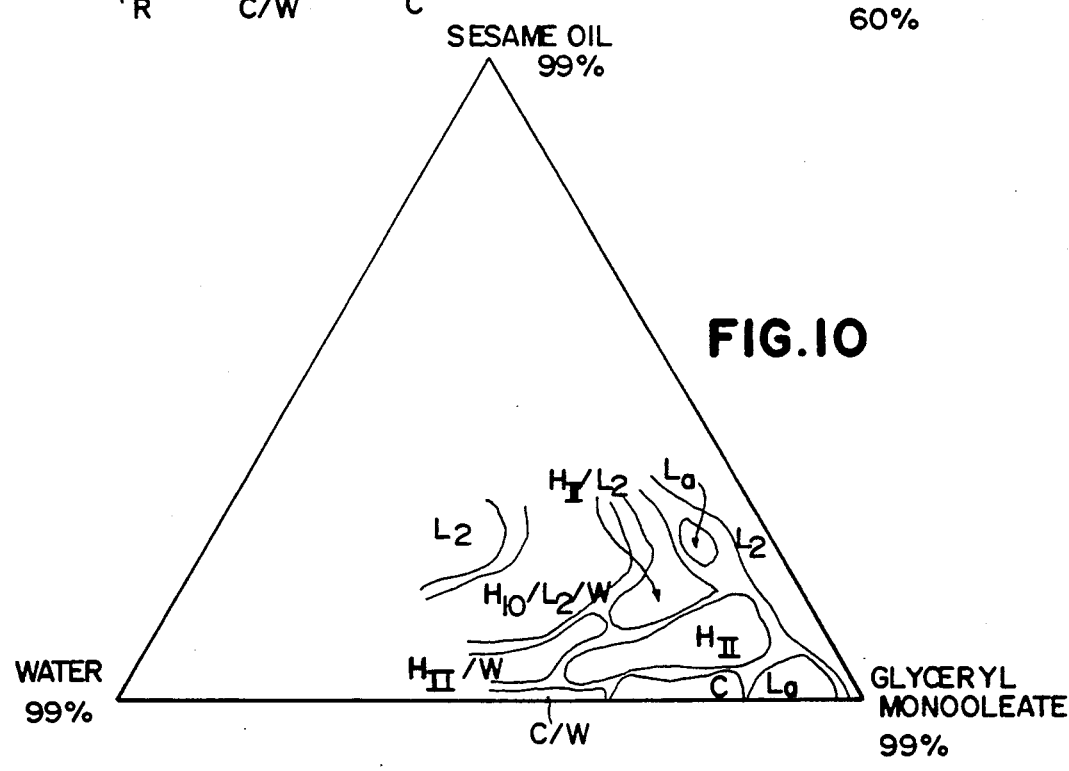
FIG. 10 is a partial three-component phase diagram created by varying the amounts of the components of a typical composition of the invention upon increasing dilution with water, while maintaining a constant drug loading (1% metronidazole).

The procedure of Example 3 was followed for a glycerol monooleate/sesame oil composition containing a drug loading of 1% metronidazole. The data is presented in the form of the partial three-component phase diagram of FIG. 10. Cubic, lamellar, reverse hexagonal and reverse micellar regions are apparent, in addition to the following two-phase regions: cubic/water (C/W), reverse hexagonal/-water ($H_{II}/W$) and reverse hexagonal/reverse micellar ($H_{II}/L_2$). A three-phase region of reverse hexagonal/-reverse micellar/water ($H_{II}/L_2/W$) is also apparent. The metronidazole benzoate in the system was completely dissolved. As in FIG. 9 (40% metronidazole benzoate loading), a relatively large region of reverse hexagonal phase is apparent.

The present invention may be embodied in other specific forms without departing from the spirit or essential attributes thereof and, accordingly, reference should be made to the appended claims, rather than to the foregoing specification, as indicating the scope of the invention.

We claim:

1. A composition for delivery of a biologically active agent to a body site in an animal or human comprising at least one monoglyceride and at least one vegetable oil, in amounts sufficient to form a reverse hexagonal liquid crystalline phase when in contact with an aqueous liquid, and an effective amount of the biologically active agent dispersed therein, said composition being a gel at about room temperature and having a melting point below about body temperature.

2. A composition according to claim 1 wherein the biologically active agent comprises metronidazole or an ester thereof.

3. A composition according to claim 1 wherein the monoglyceride is selected from the group of glycerol monooleate and glycerol monolinoleate.

4. A composition according to claim 3 wherein the vegetable oil comprises sesame oil.

5. A composition according to claim 4 wherein the biologically active agent comprises metronidazole or an ester thereof.

6. A composition according to claim 3 comprising from about 1% to about 50% by weight biologically active agent, the balance comprising a mixture of vegetable oil and monoglyceride in a weight ratio of from about 1:99 to about 30:70.

7. A composition according to claim 6 wherein the weight ratio of vegetable oil to monoglyceride is from about 1:99 to about 25:75.

8. A composition according to claim 7 wherein the weight ratio of vegetable oil to monoglyceride is from about 5:95 to about 15:85.

9. A composition according to claim 8 wherein the weight ratio of vegetable oil to monoglyceride is about 12:88, the monoglyceride comprises glycerol monooleate, and the vegetable oil comprises sesame oil.

10. A composition according to claim 9 wherein the biologically active agent comprises metronidazole or an ester thereof.

11. A composition according to claim 10 containing about 40% by weight metronidazole benzoate.

12. A composition according to claim 10 containing about 15% metronidazole by weight.

13. A composition according to claim 5 which, on contact with water and formation of the reverse hexagonal liquid crystalline phase, releases the biologically active agent in a controlled manner.

14. A method for controlled delivery of a biologically active agent to a body site in an animal or human comprising:
containing in a dosing device suitable for delivery of such agents a composition comprising an effective amount of the biologically active agent, and at least one monoglyceride and at least one vegetable oil in amounts sufficient to form a reverse hexagonal liquid crystalline phase when in contact with an aqueous liquid, said composition being a gel at about room temperature and having a melting point below about body temperature, and
discharging the composition from said dosing device into a body site wherein said composition combines with an aqueous liquid from the body site to form a reverse hexagonal liquid crystalline phase which releases the active agent to the body site in a controlled fashion.

15. A method according to claim 14 wherein the monoglyceride comprises glycerol monooleate or glycerol monolinoleate.

16. A method according to claim 15 wherein the lipid comprises glycerol monooleate.

17. A method according to claim 15 wherein the biologically active agent comprises metronidazole or ester thereof.

18. A method according to claim 13 wherein the body site comprises a periodontal pocket.

19. An article of manufacture comprising a dosing device adapted for delivery of pharmaceuticals to body sites, said dosing device containing therein a composition which is a gel at room temperature and which has a melting point below about body temperature, the composition comprising an effective amount of a biologically active agent and at least one monoglyceride and at least one vegetable oil in amounts sufficient to form a reverse hexagonal liquid crystalline phase when placed in contact with an aqueous liquid, which crystalline phase releases the active agent to the body site in a controlled manner.

20. An article according to claim 19 wherein the biologically active agent comprises metronidazole or an ester thereof.

21. A method for treating periodontal disease comprising:
delivering to a periodontal pocket of an animal or human suffering from periodontal disease a composition comprising an effective amount of a biologically active agent for the treatment of periodontal disease, at least one monoglyceride and at least one vegetable oil in amounts sufficient to form a reverse hexagonal liquid crystalline phase when placed in contact with an aqueous liquid,
combining said composition in situ in the periodontal pocket with an aqueous liquid to form a reverse hexagonal liquid crystalline phase having the biologically active agent dispersed therein, and
releasing said biologically active agent from said liquid crystalline phase in a controlled manner.

22. A method according to claim 21 wherein the composition combines with water present in body fluid from the treated subject.

23. A method according to claim 22 wherein the lipid comprises glycerol monooleate or glycerol monolinoleate.

24. A method according to claim 23 wherein the biologically active agent comprises an antibacterial agent.

25. A method according to claim 24 wherein the antibacterial agent comprises metronidazole or ester thereof.

* * * * *